(12) United States Patent
Chu et al.

(10) Patent No.: US 10,403,000 B2
(45) Date of Patent: Sep. 3, 2019

(54) METHODS AND SYSTEMS FOR ANALYZING BIOLOGICAL REACTION SYSTEMS

(71) Applicant: LIFE TECHNOLOGIES CORPORATION, Carlsbad, CA (US)

(72) Inventors: Yong Chu, Castro Valley, CA (US); Jeffrey Marks, Mountain View, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/899,308

(22) Filed: Feb. 19, 2018

(65) Prior Publication Data
US 2018/0276849 A1    Sep. 27, 2018

Related U.S. Application Data

(62) Division of application No. 14/778,415, filed as application No. PCT/US2014/031137 on Mar. 18, 2014, now Pat. No. 9,898,820.
(Continued)

(51) Int. Cl.
*G06K 9/00* (2006.01)
*G06T 5/00* (2006.01)
(Continued)

(52) U.S. Cl.
CPC .............. *G06T 7/74* (2017.01); *C12Q 1/686* (2013.01); *G06K 9/00* (2013.01); *G06T 5/002* (2013.01); *G06T 7/0012* (2013.01); *G06T 7/11* (2017.01); *G06T 7/136* (2017.01); *G06T 7/194* (2017.01); *G06K 2209/07* (2013.01); *G06T 2207/10064* (2013.01); *G06T 2207/20024* (2013.01); *G06T 2207/20208* (2013.01); *G06T 2207/30072* (2013.01)

(58) Field of Classification Search
None
See application file for complete search history.

(56) References Cited

U.S. PATENT DOCUMENTS 5,121,320 A    6/1992   Aoki
5,757,954 A    5/1998   Kuan
(Continued)

OTHER PUBLICATIONS

Rueda et al, A fully automatic gridding method for cDNA microarray images, BMC Bioinformatics 2011, 12:113.*
(Continued)

*Primary Examiner* — Andrae S Allison

(57) ABSTRACT

A method for analyzing biological reaction systems is provided. The method includes receiving an image of a substrate including a plurality of reaction sites after a biological reaction has taken place. Next, the method includes removing a noise background from the first image. The method includes determining an initial position of each reaction site based on an intensity threshold to generate a initial position set, then refining the initial position set of each reaction site based on an expected pattern of locations of the plurality of reaction sites to generate a first refined position set. The method further includes determining a presence or absence of a fluorescent emission from each reaction site based on the first refined position set and the first image.

17 Claims, 20 Drawing Sheets

Related U.S. Application Data

(60) Provisional application No. 61/827,483, filed on May 24, 2013, provisional application No. 61/803,028, filed on Mar. 18, 2013.

(51) Int. Cl.
| | |
|---|---|
| *G06T 7/00* | (2017.01) |
| *G06T 7/11* | (2017.01) |
| *G06T 7/73* | (2017.01) |
| *C12Q 1/686* | (2018.01) |
| *G06T 7/136* | (2017.01) |
| *G06T 7/194* | (2017.01) |

(56) References Cited

U.S. PATENT DOCUMENTS

| | | | | |
|---|---|---|---|---|
| 6,349,144 | B1* | 2/2002 | Shams | G06T 7/0012 |
| | | | | 382/129 |
| 6,990,221 | B2* | 1/2006 | Shams | G06T 7/0012 |
| | | | | 382/129 |
| 7,006,680 | B2* | 2/2006 | Gulati | G01N 21/253 |
| | | | | 382/133 |
| 7,171,030 | B2* | 1/2007 | Foran | G06F 19/321 |
| | | | | 382/128 |
| 7,901,887 | B2* | 3/2011 | Tafas | G01N 21/6458 |
| | | | | 435/6.12 |
| 8,009,889 | B2* | 8/2011 | Hubbell | G06K 9/00 |
| | | | | 382/128 |
| 8,055,098 | B2* | 11/2011 | Kaiser | G01N 21/6458 |
| | | | | 128/922 |
| 8,774,494 | B2* | 7/2014 | Staker | G06K 9/32 |
| | | | | 382/151 |
| 2002/0146847 | A1* | 10/2002 | Lamont | B82Y 30/00 |
| | | | | 436/518 |
| 2003/0082618 | A1* | 5/2003 | Li | C12Q 1/6809 |
| | | | | 435/6.16 |
| 2003/0138819 | A1* | 7/2003 | Gong | B01L 3/5027 |
| | | | | 435/6.11 |
| 2005/0002894 | A1* | 1/2005 | Petersohn | A61K 8/60 |
| | | | | 424/74 |
| 2005/0201602 | A1* | 9/2005 | Fenster | G06K 9/00134 |
| | | | | 382/129 |
| 2005/0239146 | A1* | 10/2005 | Tainsky | G01N 33/57411 |
| | | | | 435/7.23 |
| 2013/0323745 | A1* | 12/2013 | Wainwright | G01N 21/6486 |
| | | | | 435/6.15 |

OTHER PUBLICATIONS

G. Shao, T. Wang, Z. Chen, Y. Huang and Y. Wen, "An improved automatic gridding method for cDNA microarray images," Proceedings of the 21st International Conference on Pattern Recognition (ICPR2012), Tsukuba, 2012, pp. 1615-1618.*

Rashwan et al, A Novel Approach for Protein Spots Quantification in TwoDimensional Gel Images, International Journal of Signal Processing, Image Processing and Pattern Recognition rocessing and Pattern Recognition, vol. 4, No. 1, Mar. 2011.*

Roa et al, Real-time fluorescent image analysis of DNA spot hybridization kinetics to assess microarray spot heterogeneity, Anal Chem. Nov. 6, 2012; 84(21): 9379-9387.*

Jinn, HO et al., "Gridding Spot Centers of Smoothly Distorted Microarray Images", *IEEE Transactions on Image Processing*, vol. 15, No. 2, 2006, 342-353.

PCT/US2014/031137, International Preliminary Report on Patentability dated Oct. 1, 2015, 8 Pages.

International Search Report with Written Opinion for International Appl. No. PCT/US2014/031137 dated Jul. 15, 2014.

Rashwan, et al., "A Novel Approach for Protein Spots Quantification in TwoDimensional Gel Images", *International Journal of Signal Processing, Image Processing and Pattern Recognition*, vol. 4, No. 1, 2011.

Rueda, Luis et al., "A Fully Automatic Gridding Method for cDNA Microarray Images", *BMC Bioinformatics*, vol. 12, No. 1, 2011, 113.

Steinfath, Matthias et al., "Automated Image Analysis for Array Hybridization Experiments", *Bioinformatics*, vol. 17, No. 7, 2001, 634-641.

\* cited by examiner

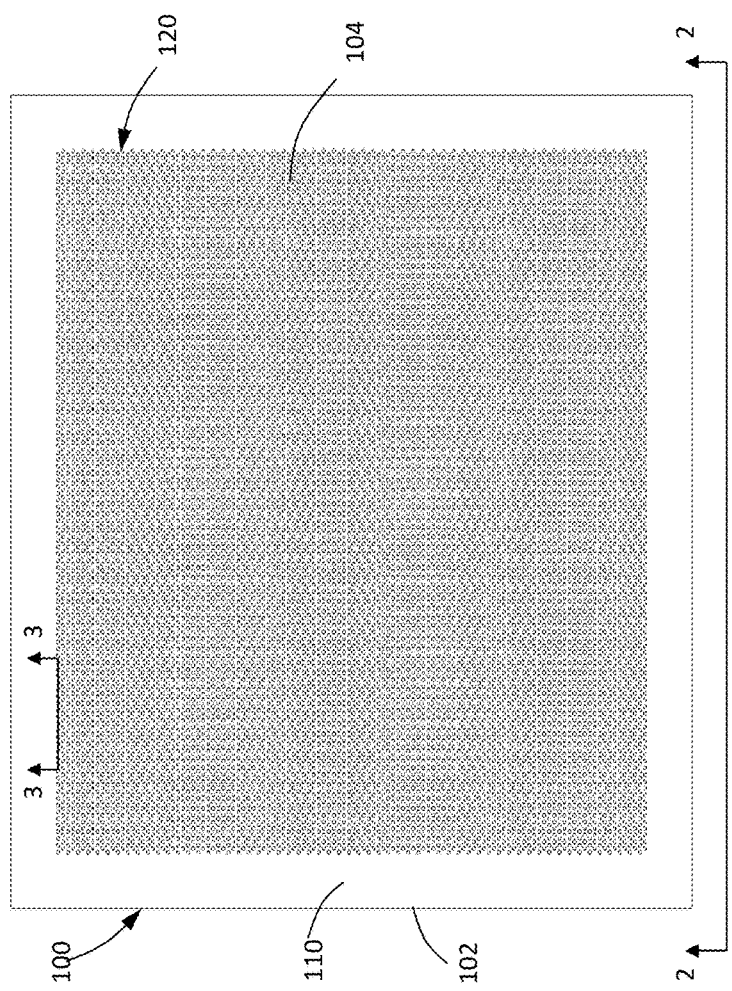
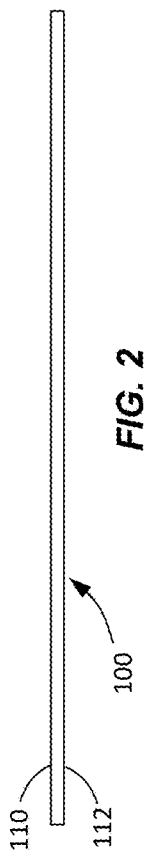
FIG. 1
FIG. 2

Enhanced ROX

Spots found on ROX

Corrected ROX

METHODS AND SYSTEMS FOR ANALYZING BIOLOGICAL REACTION SYSTEMS

CROSS-REFERENCE TO RELATED APPLICATIONS

This application is a divisional of U.S. application Ser. No. 14/778,415, filed Sep. 18, 2015, which is a 371 of PCT/US2014/031137, filed Mar. 18, 2014, which claims the benefit of Provisional Application Nos. 61/803,028, filed Mar. 18, 2013 and 61/827,483, filed May 24, 2013, all of which disclosures are herein incorporated by reference in their entirety.

BACKGROUND

The present disclosure relates to a method of treating a surface of a substrate used in a biological reaction system, and more particularly, to a method of chemically treating a surface of a substrate used in a biological reaction system to prevent biological molecules from adhering to the surface.

Polymerase Chain Reaction (PCR) is a method of amplifying a target DNA sequence. Previously, PCR has been generally performed in 96- or 384-well microplates. If higher throughputs are desired, conventional PCR methods in microplates are not cost effective or efficient. Further, in increasing throughput, reducing the PCR reaction volumes may lower the consumption of reagents, leading to a decrease in amplification times from the reduced thermal mass of the reaction volumes. This strategy may be implemented in an array format (m×n), resulting in a large number of smaller reaction volumes. Furthermore, using an array allows for a scalable high throughput analysis with increased quantification sensitivity, dynamic range, and specificity.

Arrays have also been used to perform Digital Polymerase Chain Reaction (dPCR). Results from dPCR can be used to detect and quantify the concentration of rare alleles, to provide absolute quantitation of nucleic acid samples, and to measure low fold-changes in nucleic acid concentration. Generally, increasing the number of replicates increases the accuracy and reproducibility of dPCR results.

The array format in most quantitative polymerase chain reaction (qPCR) platforms is designed for sample-by-assay experiments, in which PCR results need to be addressable for post-run analysis. For dPCR, however, the specific position or well of each PCR result may be immaterial and only the number of positive and negative replicates per sample may be analyzed.

However, accurately determining positive and negative amplification within the reaction sites is increasingly challenging with the increasing density of the reaction sites and the small volume within the reaction sites.

SUMMARY

In one exemplary embodiment, a method for analyzing biological reaction systems is provided. The method includes receiving an image of a substrate including a plurality of reaction sites after a biological reaction has taken place. Next, the method includes removing a noise background from the first image. The method includes determining an initial position of each reaction site based on an intensity threshold to generate a initial position set, then refining the initial position set of each reaction site based on an expected pattern of locations of the plurality of reaction sites to generate a first refined position set. The method further includes determining a presence or absence of a fluorescent emission from each reaction site based on the first refined position set and the first image.

DESCRIPTION OF THE FIGURES

FIG. 1 illustrates a chip including a plurality of reaction sites according to various embodiments described herein;

FIG. 2 illustrates a side view of the exemplary chip of FIG. 1 according to various embodiments described herein;

DETAILED DESCRIPTION

Figure 3:
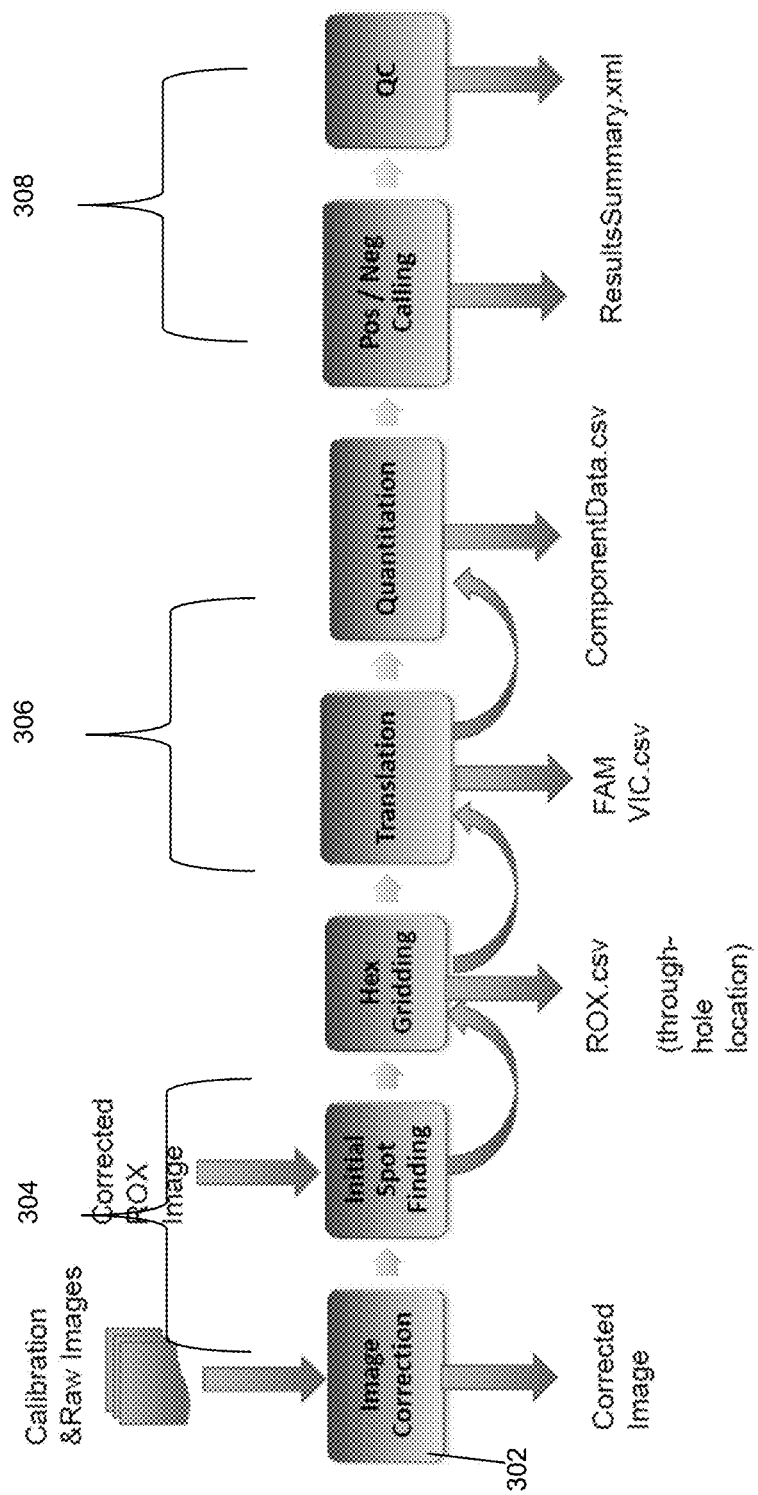
FIG. 3 illustrates a workflow for analysis of biological reaction systems according to various embodiments described herein.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

In various embodiments, the devices, instruments, systems, and methods described herein may be used to detect one or more types of biological components or targets of interest that are contained in an initial sample or solution. These biological components or targets may be any suitable biological target including, but are not limited to, DNA sequences (including cell-free DNA), RNA sequences, genes, oligonucleotides, molecules, proteins, biomarkers, cells (e.g., circulating tumor cells), or any other suitable target biomolecule. In various embodiments, such biological components may be used in conjunction with one or more PCR methods and systems in applications such as fetal diagnostics, multiplex dPCR, viral detection, quantification standards, genotyping, sequencing assays, experiments, or protocols, sequencing validation, mutation detection, detection of genetically modified organisms, rare allele detection, and/or copy number variation.

In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation. Embodiments of the present disclosure are generally directed to devices, instruments, systems, and methods for monitoring or measuring a biological reaction for a large number of small volume samples. As used herein, samples may be referred to as sample volumes, or reactions volumes, for example.

While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, cast PCR, qPCR, genome walking, and bridge PCR, for example.

As described below, in accordance with various embodiments described herein, reaction sites may include, but are not limited to, through-holes, wells, indentations, spots, cavities, sample retainment regions, and reaction chambers, for example.

Furthermore, as used herein, thermal cycling may include using a thermal cycler, isothermal amplification, thermal convention, infrared mediated thermal cycling, or helicase dependent amplification, for example. In some embodiments, the chip may be integrated with a built-in heating element. In various embodiments, the chip may be integrated with semiconductors.

According to various embodiments, detection of a target may be, but is not limited to, fluorescence detection, detection of positive or negative ions, pH detection, voltage detection, or current detection, alone or in combination, for example.

Various embodiments described herein are particularly suited for digital PCR (dPCR). In digital PCR, a solution containing a relatively small number of a target polynucleotide or nucleotide sequence may be subdivided into a large number of small test samples, such that each sample generally contains either one molecule of the target nucleotide sequence or none of the target nucleotide sequence. When the samples are subsequently thermally cycled in a PCR protocol, procedure, or experiment, the sample containing the target nucleotide sequence are amplified and produce a positive detection signal, while the samples containing no target nucleotide sequence are not amplified and produce no detection signal. Using Poisson statistics, the number of target nucleotide sequences in the original solution may be correlated to the number of samples producing a positive detection signal.

In some embodiments, the detected signal may be used to determine a number, or number range, of target molecules contained in an individual sample or volume. For example, a detection system may be configured to distinguish between samples containing one target molecule and samples containing two or at least two target molecules. Additionally or alternatively, the detection system may be configured to distinguish between samples containing a number of target molecules that is at or below a predetermined amount and samples containing more than the predetermined amount. In certain embodiments, both qPCR and dPCR processes, assays, or protocols are conducted using a single device, instrument, or system.

In certain embodiments, a dPCR protocol, assay, process, or experiment included distributing or dividing an initial sample or solution into at least ten thousand reaction sites, at least a hundred thousand reaction sites, at least one million reaction sites, or at least ten million of reaction sites. Each reaction site may have a volume of a few nanoliters, about one nanoliter, or that is less than or equal to one nanoliter (e.g., less than or equal to 100 picoliters, less than or equal to 10 picoliters, and/or less than or equal to one picoliter). When the number of target nucleotide sequences contained in the initial sample or solution is very small (e.g., less than 1000 target molecules, less than 100 target, less than 10 target molecules, or only one or two target molecules), it may also be important in certain cases that the entire content, or nearly the entire content, of the initial solution be contained in or received by the sample volumes or reaction sites being processed. For example, where there are only a few target nucleotides present in the initial solution, some or all of these target nucleotide could potentially be contained in a small residual fluid volume that are not located in any of the reaction sites and, therefore, would not be detected, measured, or counted. Thus, efficient transfer of the initial solution may aid in reducing the chances or possibility of a miscalculation in the number count of a rare allele or target nucleotide or of failing to detect the presences at all a rare allele or target nucleotide if none of the target molecules are successfully located into one of the designated reaction sites. Accordingly, embodiments of the present invention may be used to provide a high loading efficiency, where loading efficiency is defined as the volume or mass of an initial sample or solution received within the reaction sites divided by the total volume or mass of the initial sample or solution.

Embodiments described herein solve these and other dPCR design constraints by distributing an initial sample solution into a plurality of reaction sites in a way that accounts for all, or essentially all, of sample solution.

In various embodiments, the devices, instruments, systems, and methods described herein may be used to detect one or more types of biological components of interest. These biological components of interest may include, but are not limited to, DNA sequences, RNA sequences, genes, oligonucleotides, or cells (e.g., circulating tumor cells). In various embodiments, such biological components may be used in conjunction with various PCR, qPCR, and/or dPCR methods and systems in applications such as fetal diagnostics, multiplex dPCR, viral detection and quantification standards, genotyping, sequencing validation, mutation detection, detection of genetically modified organisms, rare allele detection, and copy number variation.

Referring to FIGS. 1-2, in certain embodiments of the present invention, an article, chip, device, substrate, slide, or plate 100 comprises a substrate 102 containing a plurality of through-holes, reaction regions, or reaction sites 104 located in substrate 102. In certain embodiments, chip 100 may comprise an article. Additionally or alternatively, chip 100 may comprise a microfluidic device which, for example, may further include a plurality of channels or paths for transferring reagents and/or test solutions to reaction sites 104. In other embodiments, reaction sites 104 comprise a plurality of droplets or beads and chip 100 may comprise one or more chambers and/or channels containing some or all of the droplets or beads 104. In such embodiments, droplets or beads 104 may form an emulsion, where some or all of droplets or beads 104 contain one or more target of at least one polynucleotide or nucleotide sequence. Where reaction sites 104 are beads, the beams may optionally include an attached optical signature or label. Droplets or beams 104 may be inspected, monitored, or measured either one at time or in groups containing one or more droplets or beads 104, for example using an imaging system according to embodiments of the present invention.

In the illustrated embodiment, chip 100 comprises a first surface 110 and an opposing second surface 112. In the illustrated embodiment, each reaction site 104 extends from an opening 114 in first surface 110 to an opening 116 in second surface 112. In a various embodiments, reaction sites comprise through-holes. For example, reaction sites 104 may include reaction volumes located within wells or indentations formed in substrate 102, spots of solution distributed on the surfaces 110 or 112, or other types of reaction chambers or formats, such as samples or solutions located within test sites or volumes of a microfluidic system, or within or on small beads or spheres.

Reaction sites 104 may be configured to provide sufficient surface tension by capillary action to draw in respective amounts of liquid or sample containing a biological components of interest. Chip 100 may have a general form or construction as disclosed in any of U.S. Pat. No. 6,306,578; 7,332,271; 7,604,983; 7,6825,65; 6,387,331; or 6,893,877, which are herein incorporated by reference in their entirety as if fully set forth herein. Substrate 102 may be a flat plate or comprise any form suitable for a particular application, assay, or experiment. Substrate 102 may comprise any of the various materials known in the fabrication arts including, but not limited to, a metal, glass, ceramic, silicon, or the like. Additionally or alternatively, substrate 102 may comprise a polymer material such as an acrylic, styrene, polyethylene, polycarbonate, and polypropylene material. Substrate 102 and reaction sites 104 may be formed by one or more of machining, injection molding, hot embossing, laser drilling, photolithography, or the like.

In certain embodiments, surfaces 110, 112 may comprise a hydrophobic material, for example, as described in US Patent Application Publication Numbers 2006/0057209 or 2006/0105453, which are herein incorporated by reference in their entirety as if fully set forth herein. In such embodiments, reaction sites 104 may comprise a hydrophilic material that attracts water or other liquid solutions. An array of such hydrophilic regions may comprise hydrophilic islands on a hydrophobic surface and may be formed on or within substrate 102 using any of various micro-fabrication techniques including, but are not limited to, depositions, plasmas, masking methods, transfer printing, screen printing, spotting, or the like.

It has been discovered that a high reaction site density may be configured to reduce the amount of a solution that is left on surface 110, 112 during a loading process, thus leading to higher loading efficiency or transfer of the initial solution. For example, by reducing ratio of the value of the spacing between adjacent well to the value of the well diameter, the amount of solution left on the surface of a plate may be significantly reduced so that, all, or nearly all, of an initial solution or sample containing biological components of interest is located inside reaction sites 104. In this way the possibility is reduced of missing a rare allele or other target molecule, since it would be less likely that one or more target molecule would remain on the substrate After a biological reaction, the results are detected. In various embodiments, detection includes detecting fluorescence, or the absence of fluorescence from the plurality of reaction sites. In various embodiments, the substrate, including the plurality of reaction sites, is imaged. A processor may execute instructions to determine locations of the plurality of reaction site and corresponding fluorescent emissions, if any, from each reaction site for further analysis.

An exemplary workflow is illustrated in FIG. 3. To determine whether a reaction site has fluorescent emissions (positive), or has an absence of fluorescent emissions (negative), a plurality of image corrections, calibrations, and adjustment are made by a processor to accurately detect if a reaction site is positive or negative. As described above, determining the number of negative reaction sites may be used to quantify the number of molecules in a sample, which can be used in further analysis. Steps that may be taken in a workflow, according to various embodiments, include image correction 302, spotfinding 304, quantitation 306, and color calling 308.

Figure 4:
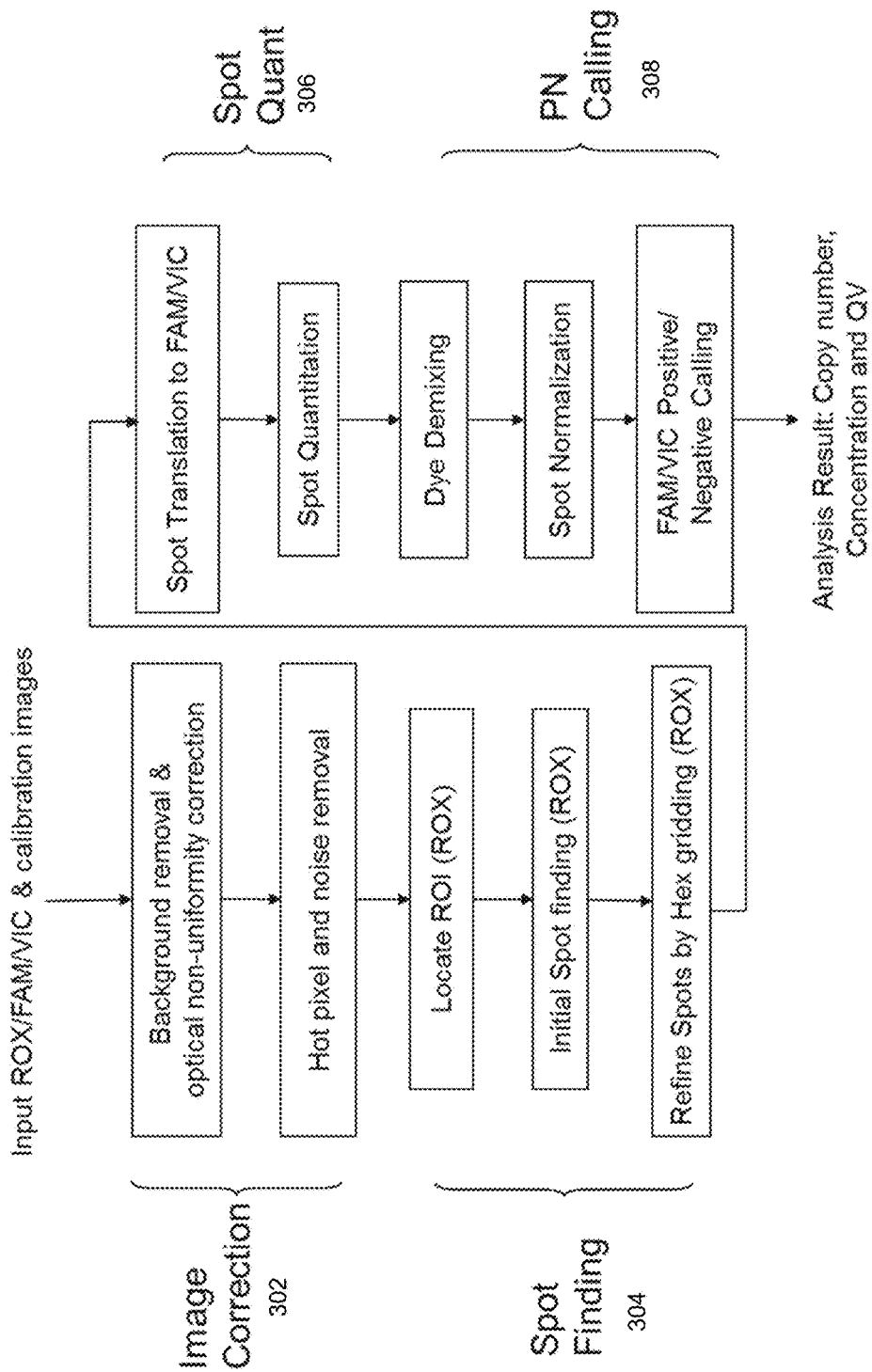
FIG. 4 illustrates a workflow for analysis of biological reaction systems according to various embodiments described herein.

A more detailed workflow is shown in FIG. 4. The workflow begins with an input of raw images of a substrate including the plurality of reaction sites. According to various embodiments, the first step in the exemplary workflow is image correction.

Image Correction

With reference to FIG. 4, in the image correction step 302, the background of the image is removed. The background removal may include subtracting dark images from the raw images. There may be more than one raw image. There may be a plurality of detectors to detect emissions from a plurality of fluorescent dyes. For example, there may be a ROX, FAM, and/or VIC images showing ROX, FAM, and/or VIC emissions, respectively.

As such, dark calibration images may be subtracted from the raw images. Further, pixels that may be errors and other noise can be removed by median filtering the raw image data, also included in step 302.

Further, step 302 includes removal of optical non-uniformity due to errors propagated by the optical system. This can be corrected by using uniformity images.

Figure 5B:
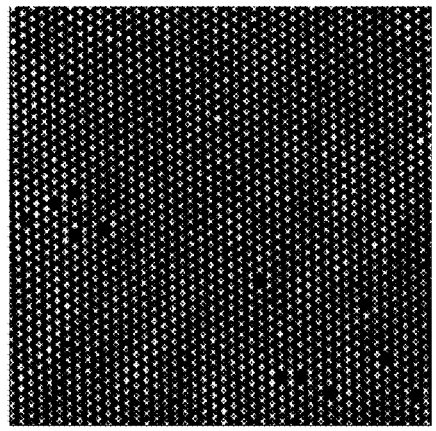
FIG. 5B illustrates an enhanced ROX image according to various embodiments described herein.
Figure 5C:
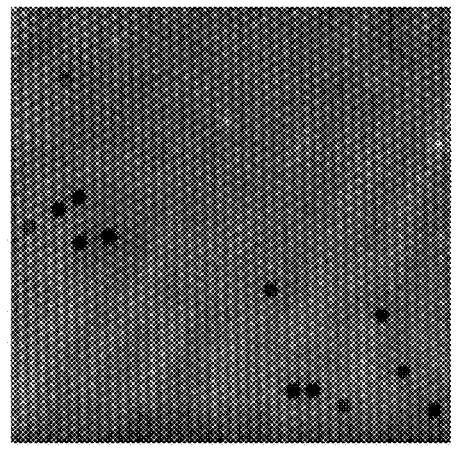
FIG. 5C illustrates the reaction site determinations according to various embodiments described herein.
Figure 5A:
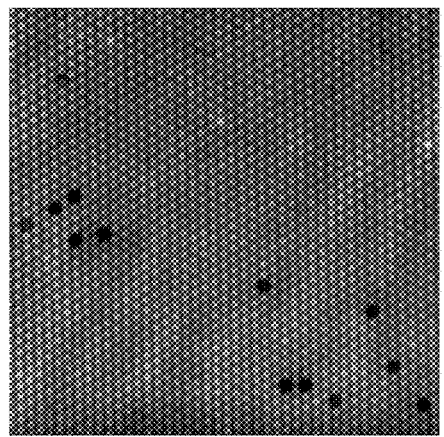
FIG. 5A illustrates a corrected ROX image according to various embodiments described herein.

An example of an image corrected image is shown in FIG. 5A.

Spot Finding

With reference back to FIG. 4, the workflow includes a spot finding step 304, according to various embodiments. In the spot finding step 304, the locations of the reactions sites of the chip filled with a sample volume are determined in the image. In other words, the image data that corresponds to reaction sites are determined so that the data can be further analyzed according to various embodiments. By determining the image data that corresponds to a reaction site, the data may be analyzed to determine if any fluorescent emissions due to amplification are detected from the reaction site. As mentioned above, the presence or absence of fluorescence may indicate a presence or absence of a target molecule in a biological sample included within the reaction site.

Spot finding step 304 includes steps of locating a Region-Of-Interest (ROI), performing initial spot finding, and refining the determined location of spots by gridding.

Determining ROIs

As mentioned above, the ROI within an image is located to begin spot finding 304. The corrected image data is then used to determine where the spots (reaction sites) are located within the image. The image includes an image of the whole substrate including the plurality of reaction sites. As such, the image may include portions of the substrate that do not include reaction sites, or the apparatus the substrate is resting on when the image is taken, for example. The region of interest (ROI) includes the portion of substrate that includes the plurality of reaction sites used in a biological reaction. The ROI may be determined by determining the background and foreground of an image. The foreground will contain the portion of the image including the ROI. The background may include the portions of the substrate that do not include reaction sites. The distinction between the background and foreground may be accomplished by a thresholding method, such as Ostu thresholding, for example.

According to various embodiments, the two largest ROIs may be determined to analyze. By using the two largest ROIs, it is likely that substantially all of the plurality of reaction sites are included and can be used for further analysis.

Additionally, another step may be taken before finding the ROI to remove portions of the image that may be affected by the edge of the substrate. The edges of substrate may cause bright areas, or higher intensity areas, along the border of the substrate within the image. Thus, before determining the ROI, the edges of the substrate may be removed by excluding image data beyond a bounding box corresponding to the edges of the substrate. The ROI may be determined from the remaining image data.

Initial Spot Finding

Another step included in spot finding step 304, is the initial spot finding step, according to various embodiments. In the initial spot finding step, it is determined which image data corresponds to each reaction site, or spot. In some embodiments, ROX image data is analyzed in the initial spot finding step. Since ROX emissions may be detected from any reaction site that includes a biological sample volume. In other words, a reaction site will emit a ROX signal whether or not any target molecule is present. The reaction site merely needs to be filled with a sample volume. As such, in the initial spot finding step, the reaction sites are detected for filled reaction sites.

In various embodiments, Laplacian of Gaussian filtering is completed on the ROI within the ROX image data to enhance the image. An example of an enhanced image is shown in FIG. 5B.

Each portion of the ROI is systematically analyzed to determine the center of the reaction sites from the ROX image data. The area of each portion analyzed is based at least in part on the dimension of the chip, such as the distance between each reaction site.

In certain embodiments, 5×5 pixel portions of image data are systematically analyzed to determine an initial position set of candidate reaction site centers. In other embodiments, 7×7 pixel portions of image data are analyzed to determine an initial position set of candidate reaction site centers. As mentioned above, the area of the pixel portions is selected based on a the distance between reaction sites.

First, the pixel portions are analyzed to determine the pixel that is the local maximum of intensity. In the example of a 7×7 pixel portion, it is determined by the processor which pixel has the maximum intensity value.

Next, the value of the local maximum is compared to a predetermined threshold to determine if the value should be selected for further analysis. By thresholding, only reaction sites that meet a minimum intensity level are used for further analysis. In this way, data which may be the local maximum, but may not be filled with a sample volume, is discarded in further analysis. The local maximum of intensity values that meets an intensity threshold is initially determined to be a candidate center of a spot or reaction site. In some embodiments, Ostu thresholding is used as the thresholding method.

Refinement of Spot Positions

The next step in spot finding step 304 is analyzing the image further to refine the reaction site locations from the candidate reaction site centers found in the initial spot finding step. The initial position set may be further refined based on expected positions of the reaction sites. In various embodiments, the expected reaction site locations are arranged in a grid pattern, where each reaction site has an expected set of coordinates. According to various embodiments, the expected grid and the image may not be exactly aligned due to various factors such as optical distortion or slight movement of the chip. As such, the relationship between the expected grid pattern and image is determined by a mapping function. By applying a mapping function to the xy locations in the image, the corresponding reaction sites in the expected grid may be determined. In other words, the expected location of a reaction site may be matched to the corresponding image data within the image using the mapping function.

As mentioned above, the positions of the reaction sites are expected from the pattern of the reaction sites in the substrate. For example, the layout of the reaction sites in a substrate may be in a hexagonal pattern. Thus, in refining the initial position set, the expected pattern of reaction sites in relation to a neighboring reaction site may be used to further refine the location of the reaction site within the image. In other words, the surrounding pixels may be searched to find the next reaction site based on the expected location of the neighboring reaction site.

In the example where the reaction sites are arranged in a hexagonal pattern according to various embodiments, looking at one reaction site, it can be expected that there should be six neighboring reaction sites at a distance of 6-8 pixels based on the dimensions of the chip.

Figure 6B:
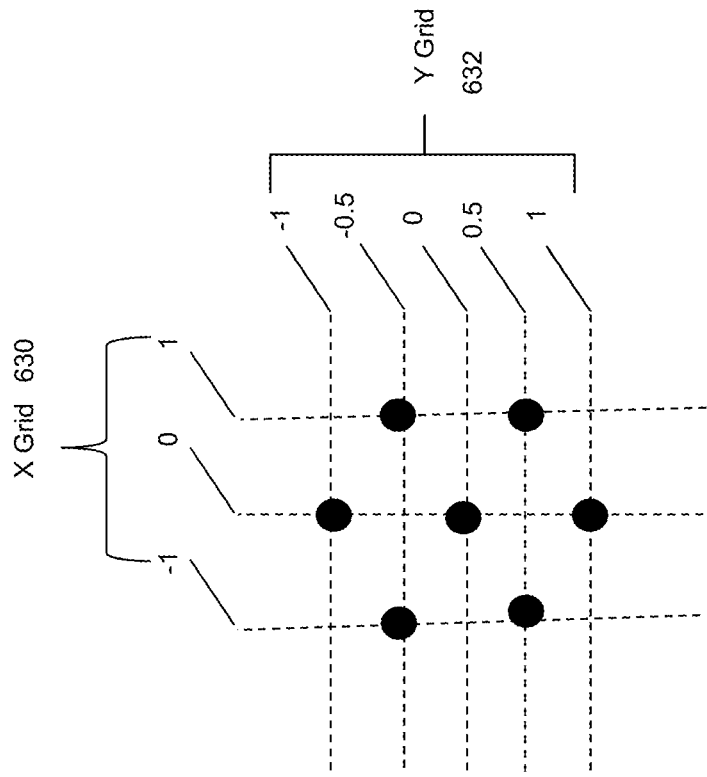
FIG. 6B illustrates a group of reaction sites in a vertical orientation in an x-y grid according to various embodiments described herein.
Figure 6A:
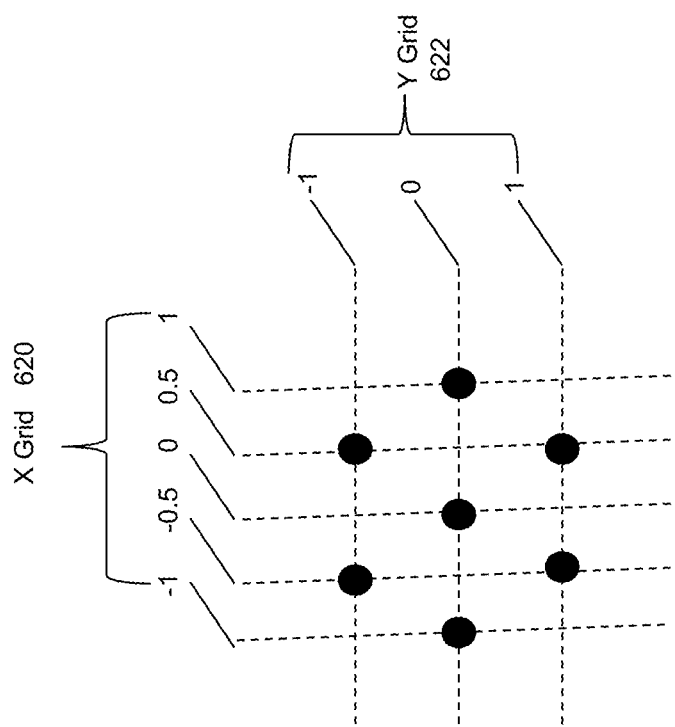
FIG. 6A illustrates a group of reaction sites in a horizontal orientation in an x-y grid according to various embodiments described herein.
Figure 6D:
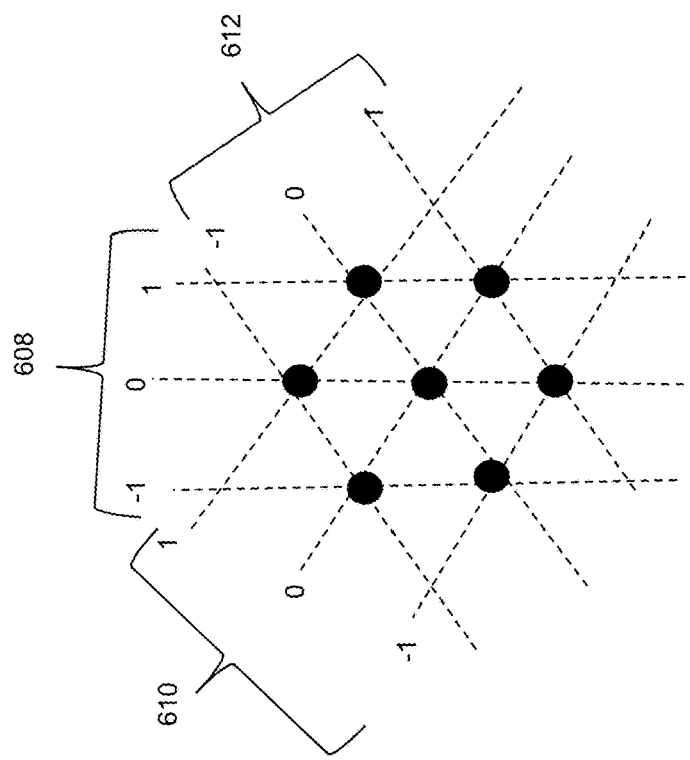
FIG. 6D illustrates a hexagonal pattern of reaction sites in a vertical orientation according to various embodiments described herein.
Figure 6C:
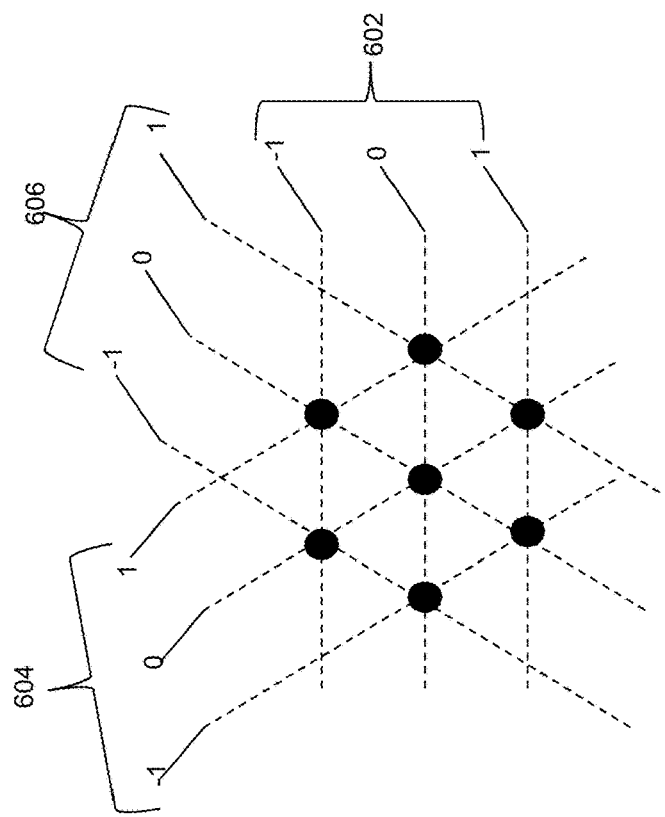
FIG. 6C illustrates a hexagonal pattern of reaction sites in a horizontal orientation according to various embodiments described herein.

With reference to FIG. 6A, an x-y coordinate system may be applied to reaction sites in a hexagonal pattern. The orientation of the reaction sites is horizontal. As shown, the reaction sites each have an x-axis 620 and a y-axis 622. Similarly, a coordinate system using three axes may be used to identify the reaction sites in a horizontal orientation, as shown in FIG. 6C. For example, the pattern in FIG. 6C has 3 axes, axis 1 602, axis 2 604, and axis 3, 606.

With reference to FIG. 6B, an x-y coordinate system may be applied to reaction sites in a hexagonal pattern. The orientation of the reaction sites is vertical. As shown, the reaction sites each have an x-axis 630 and a y-axis 632. Similarly, a coordinate system using three axes may be used to identify the reaction sites in a horizontal orientation, as shown in FIG. 6D. For example, the pattern in FIG. 6D has 3 axes, axis 1 608, axis 2 610, and axis 3, 612. The relationship between the hexagonal axes (FIGS. 6C and 6D) to the x-y grids (FIGS. 6A and 6B) can be expressed by the following equations:

$$axis1 = ygrid$$

$$axis2 = ygrid*0.5 - xgrid$$

$$axis3 = ygrid*0.5 + xgrid$$

According to embodiments using the xy grids as show in FIGS. 6A and 6B, the grids may be expanded to map to the positions positions for reaction sites past the immediate neighboring reaction sites based on the expected pattern.

As shown in FIGS. 6A-6D, the delta x values from a reaction site center to each of the neighboring reactions sites may be determined by a processor. If the sum of the delta x values (the sum of delta x values from a reaction site center to each of the 6 neighboring reaction sites) is under 3 pixels and the sum of the delta y values (the sum of delta y values from a reaction site center to each of the 6 neighboring reaction sites) is under 3 pixels, then the candidate reaction site center is determined to be a reaction site center used to derive the mapping function.

Next, the orientation of the determined reaction site center is determined. In the hexagonal reaction site arrangement example, as shown in FIG. 6A, the reaction site center may have been determined in a horizontal or vertical orientation. In each grouping of seven reaction sites (1 center with 6 neighboring reaction sites), there is a x distance and a y distance between each of these reaction sites. A horizontal orientation may be determined if the maximum x distance between two reaction sites is greater than the max distance between reaction sites in the y direction, as shown in FIG. 6A. On the other hand, in the group of seven reaction sites, if the y maximum distance between two reaction sites is greater than the maximum distance in the x-direction, then the orientation is determined to be in the vertical orientation, as shown in FIG. 6B.

The mapping function is determined by using the reaction site centers determined to be in the same orientation. In some embodiments, at least 10% of the candidate reaction site centers should be selected for a valid image.

Figure 7:
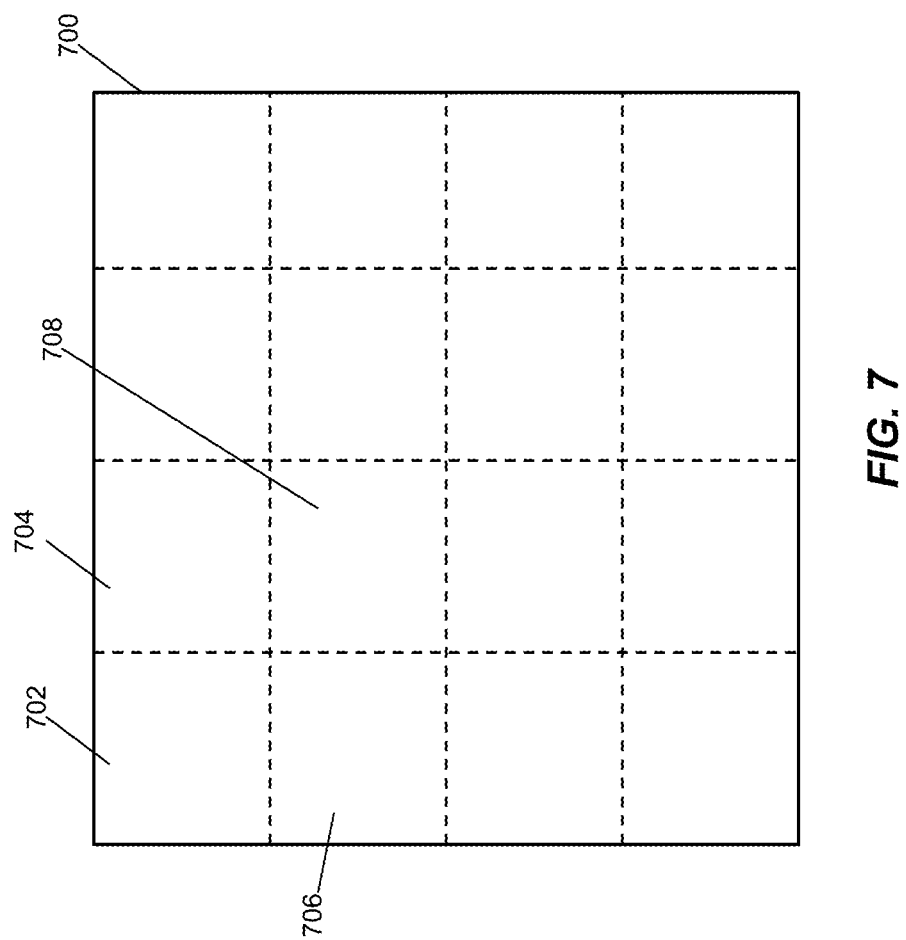
FIG. 7 illustrates a Region-Of-Interest (ROI) divided into a plurality of subregions for analysis according to various embodiments described herein.

Next, the ROI is divided into a plurality of subregions. In various embodiments, a subregion may comprise 160×160 pixels. FIG. 7 illustrates ROI 700 divided into a plurality of subregions 702, 704, 706, and 708.

For each subregion, an origin is selected by determining which candidate spot center has the smallest delta x and smallest delta y between its neighboring reaction sites. Using the reaction site selected as the origin for the subregion, the other reaction sites within the subregion are assigned x-y coordinates to determine the grid. By comparing the reaction site locations within an the image and the expected grid, the mapping function is generated by the processor. The mapping function is generated by using the point pairs of the reaction sites to computer an initial transformation estimate with a simple least-squares scheme. Then, the Levenberg-Marquardt method may be applied to reduce the re-projection error according to various embodiments. The mapping function takes into account the scale, x-y translation, and optical distortion, for example. By applying the mapping function, refined reaction site locations are determined.

Next, scores based on the distance of the grids to the origin of each subregion are calculated based on the following equation:

$$s = (-2^2/2 \cdot D^2)$$

where s is the score, d is the distance form the origin to the reaction site being scored, and D is the length of the subregion. In the example described above, D is 160 pixels.

Next, the grids of each subregion are aligned. Only grids with good scores are used in the alignment function. A good score, according to various embodiments are scores that are greater than $e^{-1}$. An offset table is generated to define the grid offset for each subregion. The grids that assign coordinates of a reaction site within 1 pixel of the same reaction site are used to calculate the offset. The grid offset table is used to update grids and recalculate the XY locations based on the grids and their score. The grids that do not align are removed.

Thus, analyzing the image data of different subregions within the ROI may result in different x-y position estimations for a particular reaction site. In these instances, a score, based on the distance from the particular reaction whose locations to a subregion, is used to calculate by the processor the best location estimation for the reaction site. In other words, a location estimation of a particular reaction site based on a reaction site in close proximity to the particular reaction site may have a higher score than the location estimation of the particular reaction site based on a reaction site located further away. The location of the particular reaction site based on the reaction site in close proximity is most likely more accurate. Thus, the final location of the particular reaction site determined by a weighted average of all estimations, where the weights are defined by the scores of those location estimations.

An example of refinement of reaction site locations is illustrated in FIG. 5C.

Spot Translation

In the next step, the refined position set for the plurality of reaction sites may be further translated to another image. For example, the initial and refined position set described above may be translated to the image data from a FAM/VIC image. The locations of reaction sites in a ROX image need to be matched to the corresponding reaction sites in FAM/VIC images. A transform matrix may be applied to the refined position set to account for the translation shift, scaling and rotation between the ROX image and FAM/VIC images In some embodiments, the x-y translation shift should not be greater than 3 pixels. If xy translation shift >3 pixels, an image alignment algorithm is used to calculate XY translation based on phase shift in in Discrete Fourier domain (could be up to 20 pixels)

Positive/Negative Calling

According to various embodiments, the method for analyzing biological reaction systems may also include dye demixing. This may also be referred to as dye deconvolution.

After determining the reaction site locations within the image, a determination of whether there is fluorescent emissions, from a reaction site (positive call) or there is an absence of fluorescent emissions from a reaction site (negative call) can be determined based on intensities of the pixels. This may be accomplished by Ostu thresholding. Various levels of thresholding may be used to make the positive and negative determinations.

According to various embodiments described herein, color calling may be determined by using a histogram of the intensity values of the determine reaction site portions of the image. According to various embodiments, the histogram is calculated for the FAM/VIC signals of the plurality of reaction sites, the cumulative distribution curve is constructed from the histogram, the cumulative curve is approximated by the Douglas-Peuker algorithm, the cumulative distribution curve is reconstructed from the approximation, and the derivative of the cumulative curve is taken to generate a smoothed histogram. In this way, in removing noise from the curve, information loss is minimized.

Figure 8A:
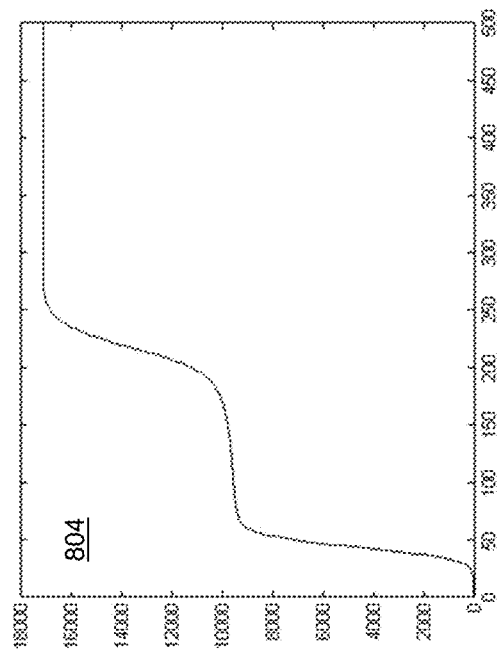
FIG. 8A illustrates a histogram of intensity values or reaction sites in an image according to various embodiments described herein.
Figure 8B:
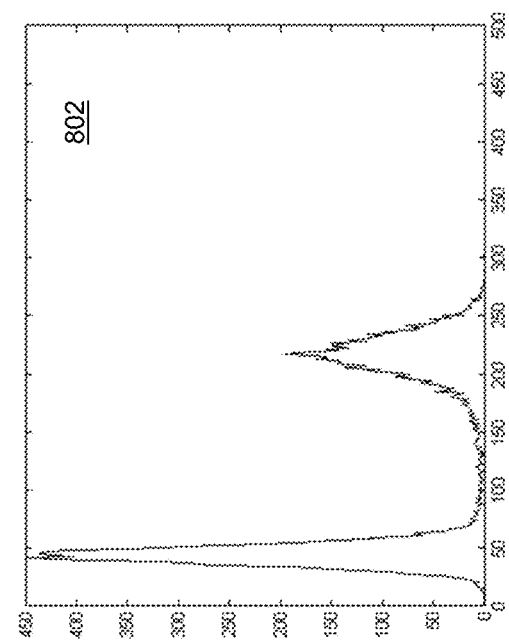
FIG. 8B illustrates a cumulative curve of the histogram of FIG. 8A according to various embodiments described herein.
Figure 9:
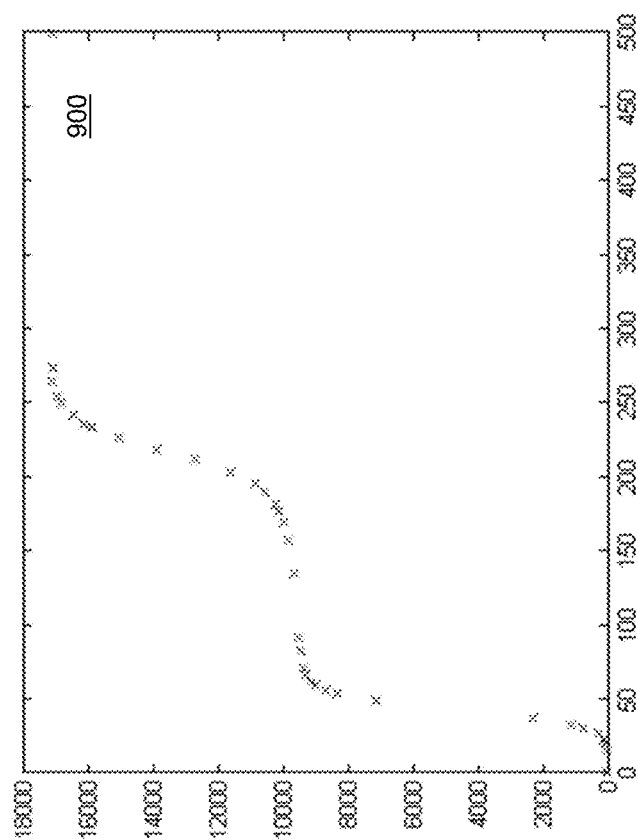
FIG. 9 illustrates a curve approximation of the cumulative curve of FIG. 8B according to various embodiments described herein.
Figure 10A:
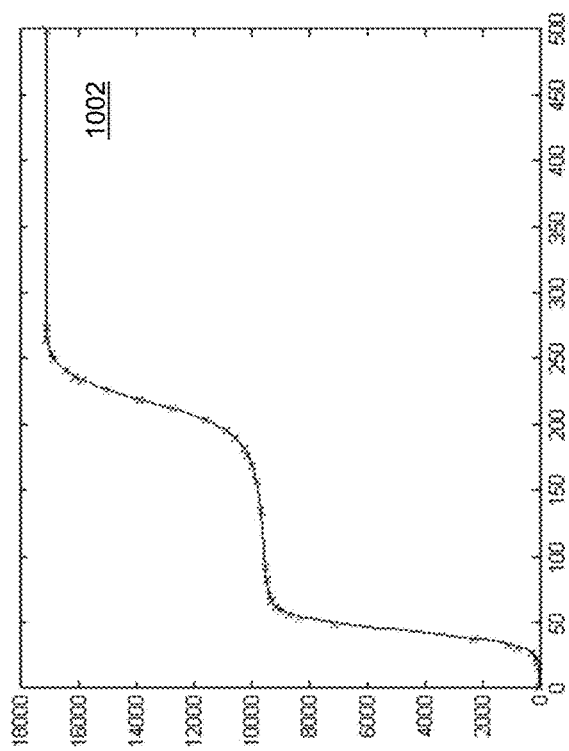
FIG. 10A illustrates a reconstructed cumulative distribution curve according to various embodiments described herein.
Figure 10B:
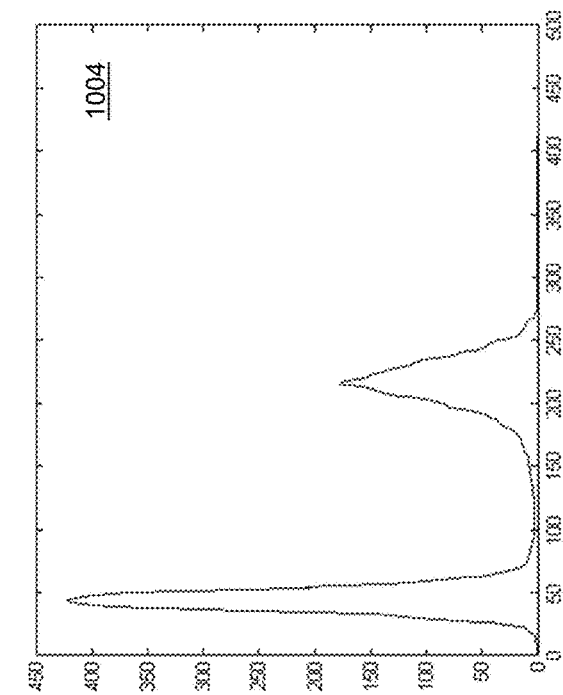
FIG. 10B illustrates a smoothed histogram curve according to various embodiments described herein.

FIG. 8A illustrates a histogram of intensity values or reaction sites in an image. FIG. 8B illustrates a cumulative curve of the histogram of FIG. 8A according to various embodiments described herein. FIG. 9 illustrates a curve approximation of the cumulative curve of FIG. 8B according to various embodiments described herein. FIG. 10A illustrates a reconstructed cumulative distribution curve according to various embodiments described herein. FIG. 10B illustrates a smoothed histogram curve according to various embodiments described herein.

Figure 11B:
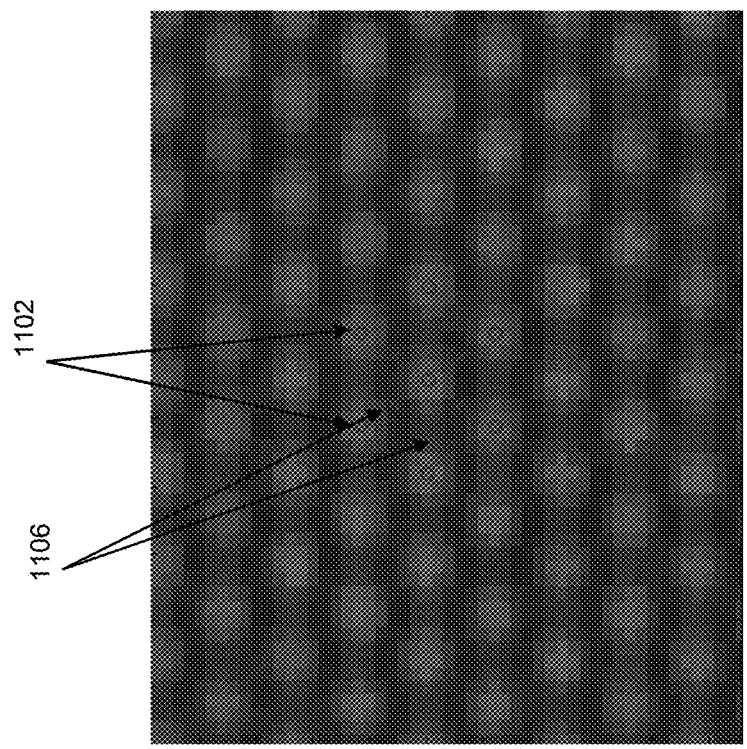
FIG. 11B illustrates another example of spacer and spot indications to determine contrast in an images according to various embodiments described herein.
Figure 11A:
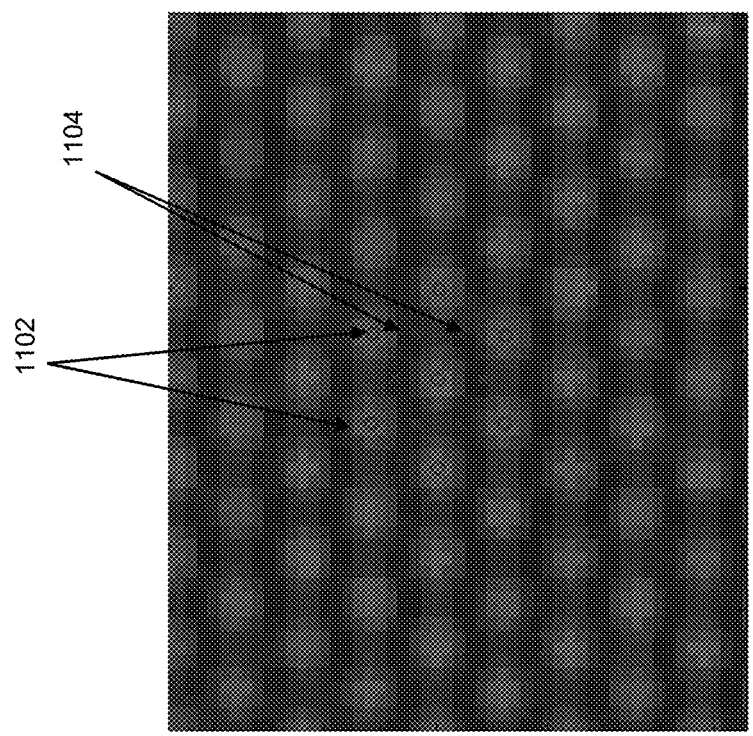
FIG. 11A illustrates an example of spacer and spot indications to determine contrast in an images according to various embodiments described herein.

FIG. 11A illustrates an example of spacer and spot indications to determine contrast in an images according to various embodiments described herein. Spots indicate the reaction sites. Spots 1102 are shown in FIGS. 11A and 11B. Furthermore, spacers are also determined and indicated in FIGS. 11A and 11B. The first set of spacer 1104 (Spacer 1) are illustrated in FIG. 11A. The second set of spacers 1106 (Spacers 2) are illustrated in FIG. 11B. Spacers 1104 and 1106 may be determined by finding the center between spots 1102, for example. Indicating spots 1102 and spacers 1104 and 1106 may be used to determine a quality value of data. Low quality values indicate errors and may be excluded from further analysis in various embodiments.

Hole level quality values may be determined by the following:

$$QV \text{ Contrast } 1([0, 1] \text{ range}): \left(H - \max_{S_i \in Spacer1}(S_i)\right)/H$$

$$QV \text{ Contrast } 2([0, 1] \text{ range}): \left(H - \max_{S_i \in Spacer2}(S_i)\right)/H$$

Figure 12:
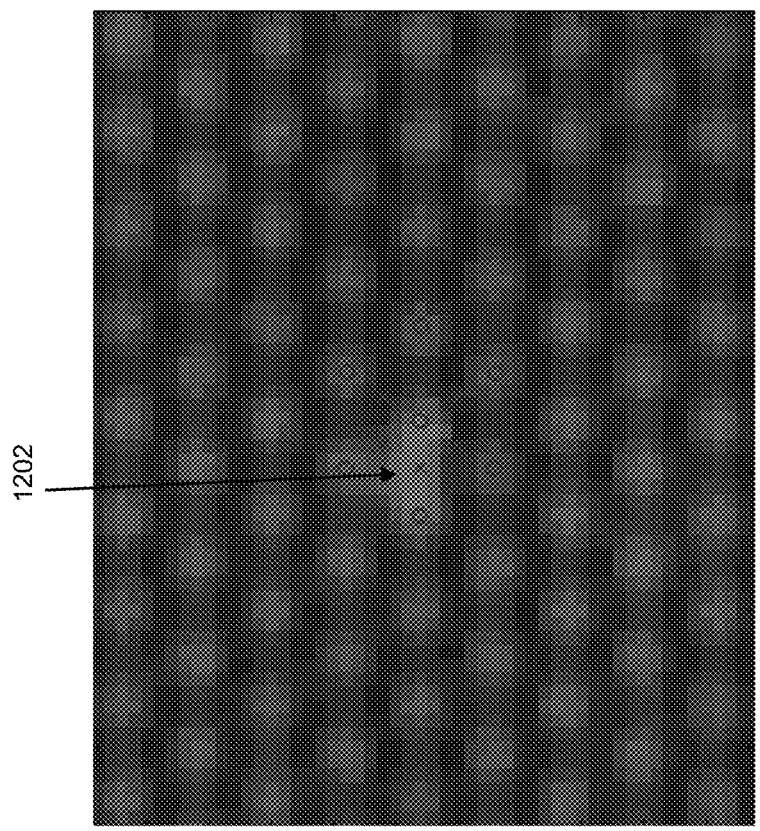
FIG. 12 illustrates a low contrast portion of an image according to various embodiments described herein.
Figure 13:
FIG. 13 illustrates debris in the image according to various embodiments described herein.

For example, some portions of an image may have low contrast and a low quality value, as illustrated in FIG. 12. Another situation where a quality value in an image may be low is if there is debris on the substrate that was imaged. FIG. 13 illustrates debris 1302 in the image according to various embodiments described herein.

Figure 14:
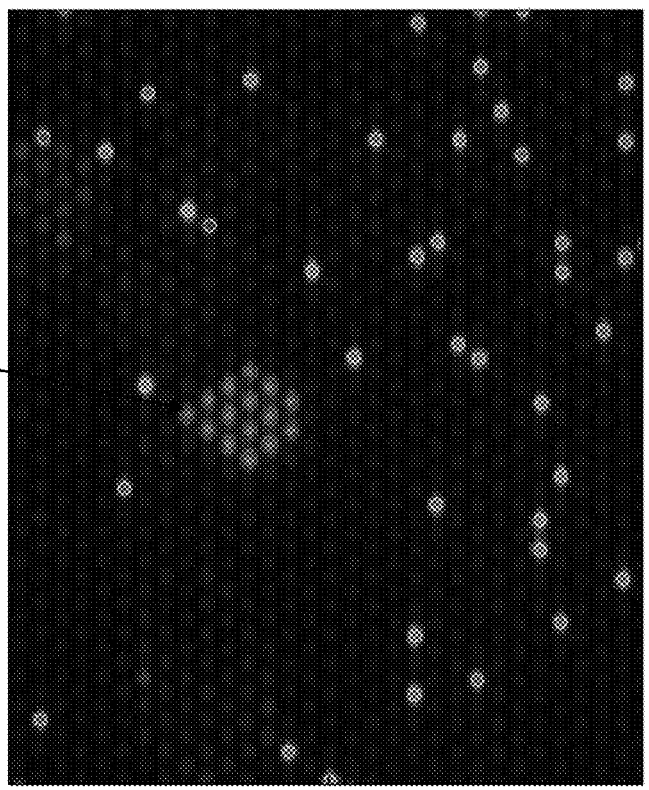
FIG. 14 illustrates positive call groups in an image according to various embodiments described herein.
Figure 15:
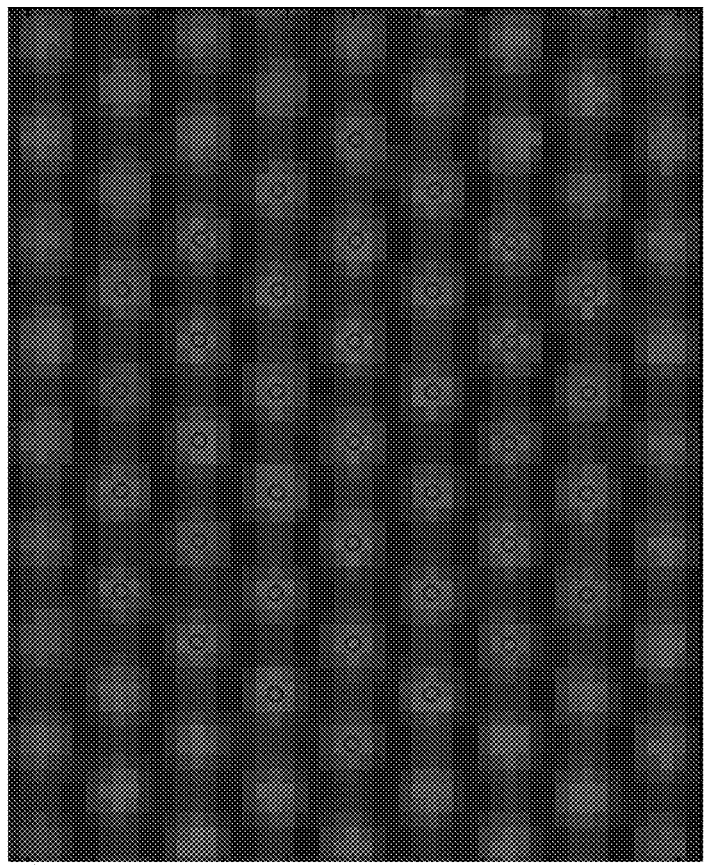
FIG. 15 illustrates local positive calls in an image according to various embodiments described herein.

In other situations, bridging of sample between reaction sites may occur. In other words, the sample may cross between adjacent reaction sites causing fluorescence in a group of reaction sites as illustrated by group 1402 in FIG. 14. To reduce the amount of error in further analysis due to the bridging effect, a positive group rate, the rate of positive fluorescence in local neighbors for each reaction site is determined. An image of a positive call group is illustrated in FIG. 15.

Figure 16:
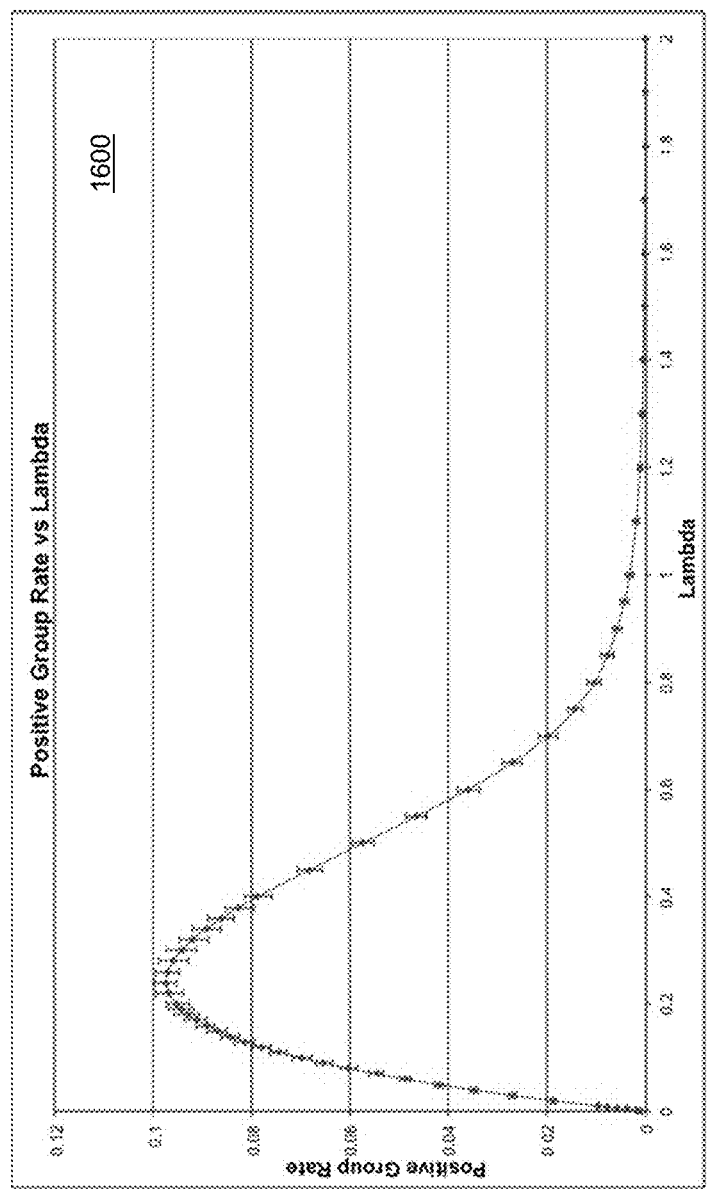
FIG. 16 illustrates a modeled positive call group rates versus lambda according to various embodiments described herein.

FIG. 16 illustrates a plot 1600 of a simulation of positive call group rates versus lambda according to various embodiments described herein. Lambda, also called multiplicity, is the average number of molecules per reaction site. By comparing the calculated group rate to the modeled group rate versus lambda, a lambda can be estimated. From lambda, the concentration of target molecules in the sample may be calculated based on Poisson statistics.

Figure 17:
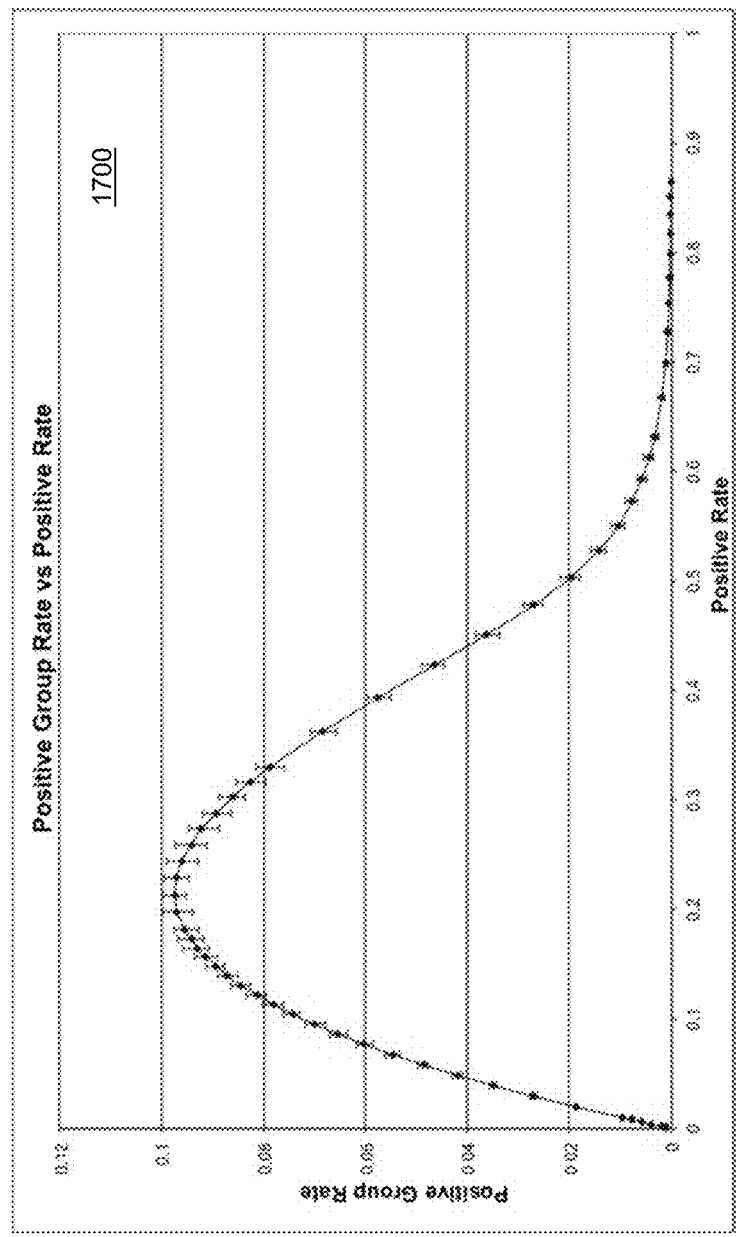
FIG. 17 illustrates a positive call group rate versus a positive call rate according to various embodiments described herein.

FIG. 17 illustrates a simulation of positive call group rate versus a positive call rate according to various embodiments described herein.

Figure 18:
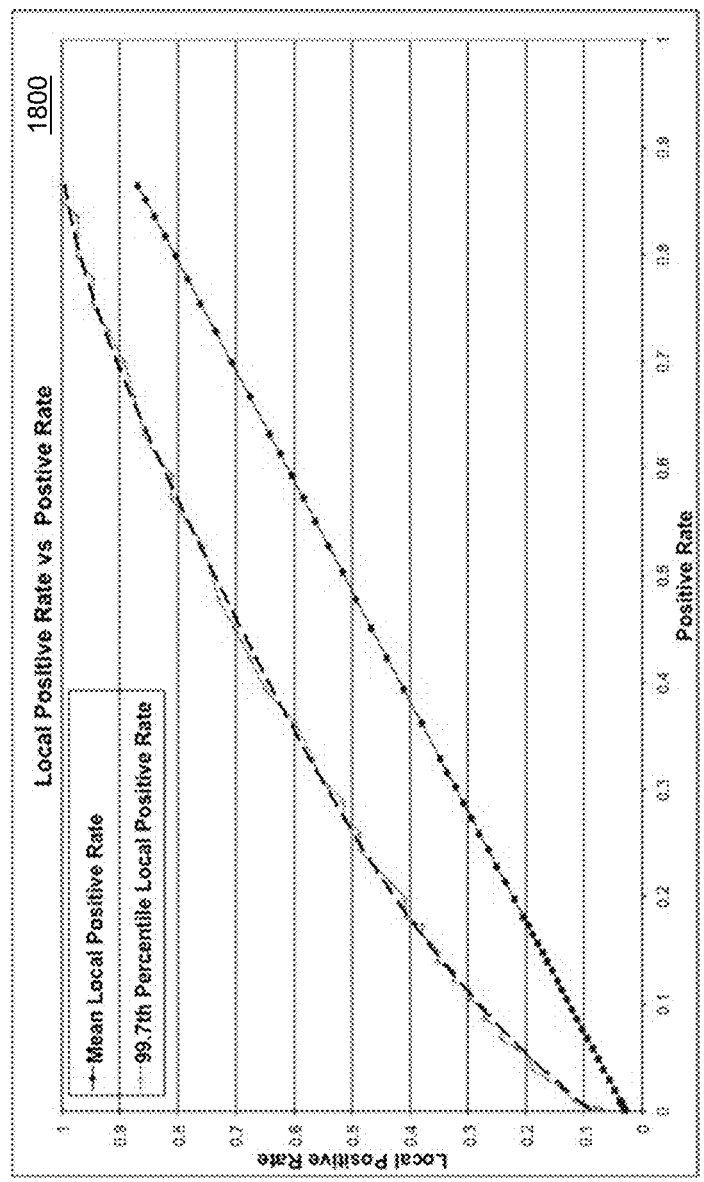
FIG. 18 illustrates a simulation of local positive call group rate versus positive call rate according to various embodiments described herein.

FIG. 18 illustrates a simulation of local positive call group rate versus positive call rate according to various embodiments described herein. The examples in FIG. 16, FIG. 17, and FIG. 18 is calculated by using one run with 19500 reaction sites, randomly assigning each reaction site to positive/negative based on the target lambda. Then the positive rate for each positive reaction site is located. The whole process is repeated by 200-1000 times. The mean and 99.7th percentile value of local positive rate are calculated.

Group Quality Value

According to various embodiments, the following may be a method for calculating a group quality value:

calculate positive rate after initial PNcalling by thresholding look up the simulation result to get the desired positive group rate and the max allowed group size (gpsize_max) based on current positive rate (only apply it on positive rate<=0.5)

re-calculate positive rate by excluding the connected group with size larger than gpsize_max from calculation.

repeat the above two steps for multiple times (up to 8 times) until all considered positive groups with size<gpsize_max look up the simulation result to get the 99.7th percentile local positive rate (locRate_max) and the desired mean of local positive rate (locRate_mean).

calculate the groupQV ([0,1] range) for each positive hole by the following equation:

(locRate_max−locRate)/(locRate_max−locRate_mean)

Metrics for Chip Level Quality Value

According to various embodiments, chip level quality value may be calculated by the following method:

Number of filled holes: nholes

Percentage of low QV:
  pctLowQV: nholes_lowQV/nholes (nholes_lowQV: the number of holes with less than QV threshold)

Median value of hole-level QV

Positive/negative Sigma Separation

Concentration: Sweet spot range (200 c/ul-2000 c/ul)

Uniformity: sort all spots by x, y and dist2edge and separate them into 8 segments. For each segments, calculate positive/negative counts. From the distribution of the positives and negatives over 8 segments, we can measure the uniformity of the distribution:

Entropy: a measure of uncertainty of random variable $$-\sum_{i=1...n} p_i \log p_i / \log n$$

Normalized Range:

$$n\left(\max_{i=1...n}(p_i) - \min_{i=1...n}(p_i)\right)$$

Whether positive rate is matched to positive group rate and locate positive rate
  isGroupMatched: yes if measured positive group rate is within 95% confidence range of expected value (based on measured positive rate), no otherwise.
  isLocalMatched: yes if measured local positive rate is within 95% confidence range of expected value (based on measured positive rate), no otherwise.
According to various embodiments, the image may be flagged with colors to indicate the chip level quality values. For example:
  Rule-based Chip QV: (table)
    nholes<5000 or PctLowQV>0.15 red
    If not red, sigmaSep<5 or Uniformity1<0.99 yellow
    everything else green
    Concentration is beyond [200 c/ul-2000 c/ul]

can be implemented using a general or special purpose processing engine such as, for example, a microprocessor, controller or other control logic. In this example, processor 1904 is connected to a bus 1902 or other communication medium.

Figure 19:
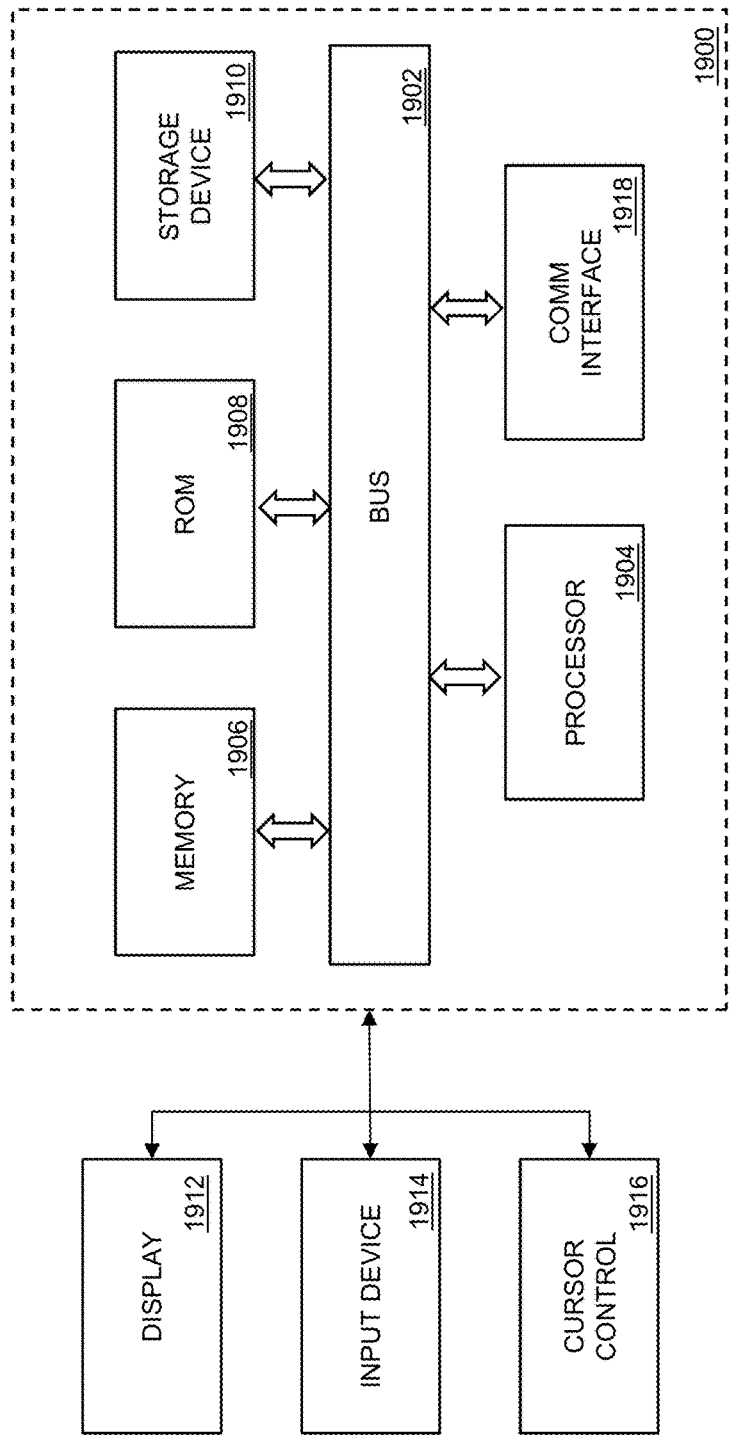
FIG. 19 illustrates an exemplary computing system that various embodiments described herein may be implemented.

Further, it should be appreciated that a computing system 1900 of FIG. 19 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1900 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 1900 may include bus 1902 or other communication mechanism for communicating information, and processor 1904 coupled with bus 1902 for processing information.

Computing system 1900 also includes a memory 1906, which can be a random access memory (RAM) or other

| Dye | Color | nholes | PctLowQV | MedianQV | SigmaSep | Uniformity1 | Uniformity2 | Concentration | isGroupMatched | isLocalMatched |
|---|---|---|---|---|---|---|---|---|---|---|
| FAM | green | 18045 | 0.00565254 | 0.812823 | 12.6937 | 0.997787 | 0.315789 | 8.11E+10 | yes | yes |
| VIC | yellow | 18045 | 0.00565254 | 0.812823 | 3.93352 | 0.965496 | 1.38879 | 3.22E+12 | no | no |

Computing System

As mentioned above, a computing system may be used to control an instrument performing the biological reactions, and an instrument detecting the results of the biological reactions. Further, an automated loading apparatus may be controlled by a computing system. The computing system may be installed in the instrument, or externally connected. Further, a computing system may also be connected to an instrument over a network. An exemplary computing system is illustrated in FIG. 19.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 20:
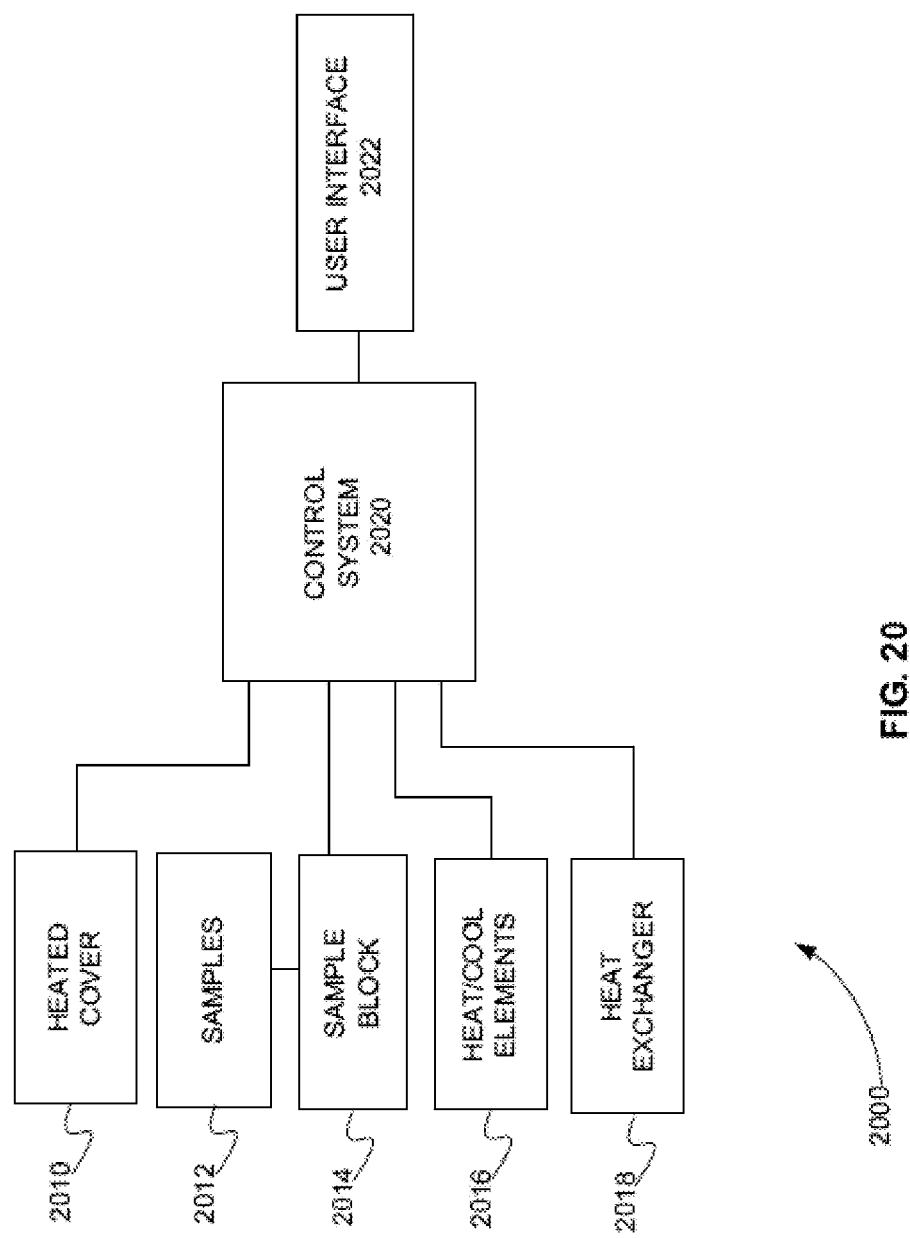
FIG. 20 illustrates a block diagram of an exemplary polymerase chain reaction instrument that may be used according to various embodiments of the present teachings.

FIG. 19 is a block diagram that illustrates a computer system 1900 that may be employed to carry out processing functionality, according to various embodiments, upon which embodiments of a thermal cycler system 2000 of FIG. 20 may utilize. Computing system 1900 can include one or more processors, such as a processor 1904. Processor 1904 can be implemented using a general or special purpose processing engine such as, for example, a microprocessor, controller or other control logic. In this example, processor 1904 is connected to a bus 1902 or other communication medium.

dynamic memory, coupled to bus 1902 for storing instructions to be executed by processor 1904. Memory 1906 also may be used for storing temporary variables or other intermediate information during execution of instructions to be executed by processor 1904. Computing system 1900 further includes a read only memory (ROM) 1908 or other static storage device coupled to bus 1902 for storing static information and instructions for processor 1904.

Computing system 1900 may also include a storage device 1910, such as a magnetic disk, optical disk, or solid state drive (SSD) is provided and coupled to bus 1902 for storing information and instructions. Storage device 1910 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1910 may include other similar instrumentalities for allowing computer programs or other instructions or data to be loaded into computing system 1900. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1910 to computing system 1900.

Computing system 1900 can also include a communications interface 1918. Communications interface 1918 can be used to allow software and data to be transferred between computing system 1900 and external devices. Examples of communications interface 1918 can include a modem, a network interface (such as an Ethernet or other NIC card), a communications port (such as for example, a USB port, a RS-232C serial port), a PCMCIA slot and card, Bluetooth, etc. Software and data transferred via communications interface 1918 are in the form of signals which can be electronic, electromagnetic, optical or other signals capable of being received by communications interface 1918. These signals may be transmitted and received by communications interface 1918 via a channel such as a wireless medium, wire or cable, fiber optics, or other communications medium. Some examples of a channel include a phone line, a cellular phone link, an RF link, a network interface, a local or wide area network, and other communications channels.

Computing system 1900 may be coupled via bus 1902 to a display 1912, such as a cathode ray tube (CRT) or liquid crystal display (LCD), for displaying information to a computer user. An input device 1914, including alphanumeric and other keys, is coupled to bus 1902 for communicating information and command selections to processor 1904, for example. An input device may also be a display, such as an LCD display, configured with touchscreen input capabilities. Another type of user input device is cursor control 1916, such as a mouse, a trackball or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane. A computing system 1900 provides data processing and provides a level of confidence for such data. Consistent with certain implementations of embodiments of the present teachings, data processing and confidence values are provided by computing system 1900 in response to processor 1904 executing one or more sequences of one or more instructions contained in memory 1906. Such instructions may be read into memory 1906 from another computer-readable medium, such as storage device 1910. Execution of the sequences of instructions contained in memory 1906 causes processor 1904 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1904 for execution. Such instructions, generally referred to as "computer program code" (which may be grouped in the form of computer programs or other groupings), when executed, enable the computing system 1900 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 1910. Volatile media includes dynamic memory, such as memory 1906. Transmission media includes coaxial cables, copper wire, and fiber optics, including the wires that comprise bus 1902.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1904 for execution. For example, the instructions may initially be carried on magnetic disk of a remote computer. The remote computer can load the instructions into its dynamic memory and send the instructions over a telephone line using a modem. A modem local to computing system 1900 can receive the data on the telephone line and use an infra-red transmitter to convert the data to an infra-red signal. An infra-red detector coupled to bus 1902 can receive the data carried in the infra-red signal and place the data on bus 1902. Bus 1902 carries the data to memory 1906, from which processor 1904 retrieves and executes the instructions. The instructions received by memory 1906 may optionally be stored on storage device 1910 either before or after execution by processor 1904.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.\

PCR Instrument

As mentioned above, an instrument that may be utilized according to various embodiments, but is not limited to, is a polymerase chain reaction (PCR) instrument. FIG. 20 is a block diagram that illustrates a PCR instrument 2000, upon which embodiments of the present teachings may be implemented. PCR instrument 2000 may include a heated cover 2010 that is placed over a plurality of samples 2012 contained in a sample support device (not shown). In various embodiments, a sample support device may be a glass or plastic slide with a plurality of sample regions, which sample regions have a cover between the sample regions and heated cover 2010. Some examples of a sample support device may include, but are not limited to, a multi-well plate, such as a standard microtiter 96-well, a 384-well plate, a chip illustrated in FIG. 1, or a microcard, or a substantially planar support, such as a glass or plastic slide. The sample regions in various embodiments of a sample support device may include depressions, indentations, ridges, and combinations thereof, patterned in regular or irregular arrays formed on the surface of the substrate. Various embodiments of PCR instruments include a sample block 2014, elements for heating and cooling 2016, a heat exchanger 2018, control system 2020, and user interface 2022. Various embodiments of a thermal block assembly according to the present teachings comprise components 2014-2018 of PCR instrument 2000 of FIG. 20.

For embodiments of PCR instrument 2000 in FIG. 20, control system 2020, may be used to control the functions of the detection system, heated cover, and thermal block assembly. Control system 2020 may be accessible to an end user through user interface 2022 of PCR instrument 2000 in FIG. 20. Also a computer system 1900, as depicted in FIG. 19, may serve as to provide the control the function of PCR instrument 2000 in FIG. 20, as well as the user interface function. Additionally, computer system may provide data processing, display and report preparation functions. All such instrument control functions may be dedicated locally to the PCR instrument, or a computer system may provide remote control of part or all of the control, analysis, and reporting functions.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Although various embodiments have been described with respect to certain exemplary embodiments, examples, and applications, it will be apparent to those skilled in the art that various modifications and changes may be made without departing from the present teachings.

What is claimed is:

1. A system comprising:
   a processor; and
   a memory storing instructions, executable by the processor, the instructions including instructions for:
   receiving a first image of a substrate including a plurality of reaction sites after a biological amplification reaction has taken place, wherein the biological amplification reaction increases a number of target molecules within a biological sample, and wherein the first image shows fluorescent emissions from a first dye, wherein the first dye indicates a presence of the biological sample;
   removing a noise background from the first image;
   determining an initial position of each reaction site based on an intensity threshold to generate a initial position set;
   refining the initial position set of each reaction site based on an expected pattern of locations of the plurality of reaction sites to generate a first refined position set; and
   determining a presence or absence of a fluorescent emission from each reaction site based on the first refined position set and the first image;
   receiving a second image of the substrate including a second set of reaction sites, wherein the second image shows fluorescent emissions from a second dye from the second set of reaction sites, wherein the second dye indicates a presence of a target molecule within the biological sample.

2. The system of claim 1, wherein the instructions for determining the initial position of each reaction site includes instructions for determining a local maximum of intensity values of a portion of the first image.

3. The system of claim 2, wherein the portion is a 7×7 pixel area.

4. The system of claim 1, wherein the plurality of reaction sites comprise a first set of reaction sites and a second set of reaction sites, wherein (1) the first set of reaction sites contain both the first dye and the second dye and (2) the second set of reaction sites do not contain the first dye or the second set of reaction sites do not contain the second dye.

5. A computer-implemented method for determining locations of a plurality of reaction sites on a substrate in an image, the method comprising:
   determining a set of initial reaction site locations for a plurality of reaction sites after a biological amplification reaction, from a first image of the substrate based on intensity values, wherein the biological amplification reaction increases a number of target molecules within a biological sample, and wherein the first image shows fluorescent emissions from a first dye, wherein the first dye indicates a presence of the biological sample;
   determining a set of reaction sites to be used to derive a mapping function;
   deriving the mapping function to map the determined set of initial reaction site locations to expected reaction site locations; and
   generating a set of refined reaction site locations based on the mapping function;
   determining a set of reaction sites from a second image of the substrate, wherein the second image shows fluorescent emissions from a second dye from the second set of reaction sites, wherein the second dye indicates a presence of a target molecule within the biological sample.

6. The method of claim 5, wherein determining the set of initial reaction site locations includes determining a local maximum of intensity values of a portion of the image.

7. The method of claim 6, wherein the portion is a 7×7 pixel area.

8. The method of claim 5, wherein determining the set of reaction sites to be used to derive a mapping function includes determining if a reaction site has six neighboring reaction sites within 6-8 pixels.

9. The method of claim 8, wherein determining the set of reaction sites to be used to derive the mapping function further includes determining whether an orientation of the reaction sites is the same.

10. The system of claim 5, the instructions, for emissions from at least some reaction sites in the first image and the second image, further include instructions for determining at least one of a translation shift, a rotation, or scaling change of a position in the second image relative to a corresponding position in the first image.

11. The computer-implemented method of claim 5, wherein the plurality of reaction sites comprise a first set of reaction sites and a second set of reaction sites, wherein (1) the first set of reaction sites contain both the first dye and the second dye and (2) the second set of reaction sites do not contain the first dye or the second set of reaction sites do not contain the second dye.

12. A non-transitory computer readable storage medium encoded with instructions, executable by a processor, the instructions including instructions for:
   determining a set of initial reaction site locations for a plurality of reaction sites from a first image of a substrate based on intensity values after a biological amplification reaction, wherein the first image shows fluorescent emissions from a first dye, wherein the biological amplification reaction increases a number of target molecules within a biological sample, and wherein the first dye indicates a presence of the biological sample;

determining a set of reaction sites to be used to derive a mapping function;

deriving the mapping function to map the determined set of initial reaction site locations to expected reaction site locations; and generating a set of refined reaction site locations based on the mapping function;

determining a set of reaction sites from a second image of the substrate, wherein the second image shows fluorescent emissions from a second dye from the second set of reaction sites, wherein the second dye indicates a presence of a target molecule within the biological sample.

13. The non-transitory computer readable storage medium of claim 12, wherein the instructions for determining the set of initial reaction site locations includes instructions for determining a local maximum of intensity values of a portion of the image.

14. The non-transitory computer readable storage medium of claim 13, wherein the portion is a 7×7 pixel area.

15. The non-transitory computer readable storage medium of claim 12, wherein the instructions for determining the set of reaction sites to be used to derive a mapping function includes instructions for determining if a reaction site has six neighboring reaction sites within 6-8 pixels.

16. The non-transitory computer readable storage medium of claim 15, wherein the instructions for determining the set of reaction sites to be used to derive the mapping function further includes instructions for determining whether an orientation of the reaction sites is the same.

17. The non-transitory computer readable storage medium of claim 12, wherein the plurality of reaction sites comprise a first set of reaction sites and a second set of reaction sites, wherein (1) the first set of reaction sites contain both the first dye and the second dye and (2) the second set of reaction sites do not contain the first dye or the second set of reaction sites do not contain the second dye.

\* \* \* \* \*